United States Patent
Dewdney et al.

(10) Patent No.: US 12,329,845 B2
(45) Date of Patent: Jun. 17, 2025

(54) EMULSION-BASED PERSONAL CARE COMPOSITIONS AND METHODS FOR THE SAME

(71) Applicant: Colgate-Palmolive Company, New York, NY (US)

(72) Inventors: Nadine Dewdney, Union, NJ (US); Mavis Dennis, Sayreville, NJ (US); Jodie Parker, Parsippany, NJ (US)

(73) Assignee: Colgate-Palmolive Company, New York, NY (US)

(*) Notice: Subject to any disclaimer, the term of this patent is extended or adjusted under 35 U.S.C. 154(b) by 642 days.

(21) Appl. No.: 17/250,960

(22) PCT Filed: Oct. 3, 2018

(86) PCT No.: PCT/US2018/054077
§ 371 (c)(1),
(2) Date: Apr. 2, 2021

(87) PCT Pub. No.: WO2020/072044
PCT Pub. Date: Apr. 9, 2020

(65) Prior Publication Data
US 2021/0378939 A1    Dec. 9, 2021

(51) Int. Cl.
*A61K 8/86* (2006.01)
*A61K 8/06* (2006.01)
*A61K 8/34* (2006.01)
*A61K 8/365* (2006.01)
*A61K 8/368* (2006.01)
*A61K 8/37* (2006.01)
*A61K 8/891* (2006.01)
*A61K 8/92* (2006.01)
*A61Q 19/00* (2006.01)

(52) U.S. Cl.
CPC .............. *A61K 8/86* (2013.01); *A61K 8/062* (2013.01); *A61K 8/342* (2013.01); *A61K 8/345* (2013.01); *A61K 8/365* (2013.01); *A61K 8/368* (2013.01); *A61K 8/375* (2013.01); *A61K 8/891* (2013.01); *A61K 8/92* (2013.01); *A61Q 19/007* (2013.01); *A61K 2800/30* (2013.01); *A61K 2800/524* (2013.01); *A61K 2800/5422* (2013.01)

(58) Field of Classification Search
CPC ........................................................ A61K 8/86
See application file for complete search history.

(56) References Cited

U.S. PATENT DOCUMENTS

| | | | |
|---|---|---|---|
| 4,970,216 | A | 11/1990 | Deckner et al. |
| 5,616,332 | A | 4/1997 | Herstein |
| 5,863,545 | A | 1/1999 | Griat |
| 5,976,555 | A | 11/1999 | Liu et al. |
| 6,558,680 | B1 | 5/2003 | Riedel et al. |
| 2001/0004703 | A1 | 11/2001 | McManus et al. |
| 2006/0110415 | A1 | 5/2006 | Gupta |
| 2011/0052512 | A1 | 3/2011 | Monello |

FOREIGN PATENT DOCUMENTS

| | | |
|---|---|---|
| CN | 1744877 | 3/2006 |
| EP | 0728468 | 8/1996 |
| EP | 1072247 | 1/2004 |
| RU | 2007119582 | 12/2008 |
| WO | 1996/07396 | 3/1996 |

OTHER PUBLICATIONS

Flick, E., Cosmetic and Toiletry Formulations, 2001, 2nd Ed., vol. 8, Noyes Publications William Andrew Publishing, LLC, p. 77.*
Croda, "Arlacel 165", Retrieved from the Internet on Jun. 6, 2019: URL:https://www.crodapersonalcare.com/en-gb/products-and-applications/product-finder/product/1923/Arlacel_1_165#tab-collapse-literature.
International Search Report and the Written Opinion of the International Searching Authority issued in International Application PCT/US2018/054077 mailed Jun. 27, 2019.

* cited by examiner

*Primary Examiner* — Gina C Justice

(57) ABSTRACT

Emulsion-based personal care compositions and methods for preparing the same are provided. The personal care compositions may include an emulsion of a hydrophobic phase and a hydrophilic phase. The hydrophobic phase may include an emulsifying system including a first nonionic surfactant and a second nonionic surfactant, where a weight ratio of the first nonionic surfactant to the second nonionic surfactant is from about 0.9:1 to about 1.1:1. The first nonionic surfactant may be glyceryl monostearate, and the second nonionic surfactant may be PEG-100 stearate.

13 Claims, No Drawings

EMULSION-BASED PERSONAL CARE COMPOSITIONS AND METHODS FOR THE SAME

BACKGROUND

Conventional personal care compositions, such as lotions and creams, often utilize an emulsion of a hydrophobic phase and a hydrophilic phase maintained at a generally neutral pH. For example, conventional personal care compositions may often include an emulsion of water and mineral oil to provide skin moisturizing and skin-softening effects when applied to the skin. These emulsion-based personal care compositions often utilize an emulsifying system including surfactants and emulsifiers capable of facilitating the formation of, maintaining, or stabilizing the emulsion between the hydrophobic and hydrophilic phases. As discussed above, these emulsion type personal care compositions are often maintained at a generally neutral pH, which may irritate or change the natural acidic pH of skin. The irritation of the skin may be exacerbated in infants or those with particularly sensitive skin. Efforts to reduce the pH of these emulsion-based personal care compositions, however, have not been successful, as reducing the pH of the personal care compositions often leads to instability and phase separation of the hydrophobic and hydrophilic phases thereof.

What is needed, then, are improved personal care compositions and emulsifying systems thereof, and methods for preparing and maintaining stability of the personal care composition under acidic conditions.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a personal care composition including an emulsion of a hydrophobic phase and a hydrophilic phase, wherein the hydrophobic phase includes an emulsifying system including a first nonionic surfactant and a second nonionic surfactant, wherein a weight ratio of the first nonionic surfactant to the second nonionic surfactant is from about 0.9:1 to about 1.1:1.

In at least one implementation, the first nonionic surfactant is glyceryl monostearate.

In at least one implementation, the second nonionic surfactant is PEG-100 stearate.

In at least one implementation, the glyceryl monostearate and the PEG-100 stearate are each, independently and separately, present in an amount of at least 1.5 weight %, optionally, at least 1.75 weight %, based on a total weight of the personal care composition.

In at least one implementation, the emulsifying system further includes one or more fatty alcohols, optionally, the fatty alcohols include or are selected from cetyl alcohol, stearyl alcohol, or combinations thereof, further optionally, the fatty alcohols include cetyl alcohol and cetyl-stearyl alcohol 50/50.

In at least one implementation, the emulsifying system includes the cetyl alcohol and the cetyl-stearyl alcohol 50/50, and the cetyl alcohol and the cetyl-stearyl alcohol 50/50 are present in a total amount of at least 3 weight %, optionally at least 3.5 weight %, based on a total weight of the personal care composition.

In at least one implementation, the personal care composition has an acidic pH, optionally, the pH is from about 4 to about 6, further optionally, the pH is from about 4 to about 5.

In at least one implementation, the hydrophobic phase further includes a hydrophobic liquid carrier, optionally, the hydrophobic liquid carrier includes or is selected from mineral oil, silicone oil, or combinations thereof, further optionally, the hydrophobic liquid carrier includes mineral oil and silicone oil.

In at least one implementation, the hydrophilic phase includes water.

In at least one implementation, the hydrophilic phase includes one or more preservatives, optionally, the preservatives includes or is selected from sodium benzoate, caprylyl glycol, or combinations thereof.

In at least one implementation, the hydrophilic phase includes one or more acids, optionally, the acids include lactic acid.

In at least one implementation, the personal care composition is substantially free of steric acid.

In at least one implementation, the personal care composition is substantially free of anionic surfactants.

The foregoing and/or other aspects and utilities embodied in the present disclosure may also be achieved by providing a method for preparing the personal care composition of any one of the preceding claims. The method includes emulsifying the hydrophobic phase and the hydrophilic phase with one another.

In at least one implementation, the method further includes heating the hydrophobic phase and the hydrophilic phase with one another at a temperature of about 60° C. to about 90° C., optionally about 70° C. to about 80° C., further optionally about 70° C. to about 75° C.

In at least one implementation, the method includes maintaining a pH of from about 4 to about 5.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout this disclosure, ranges are used as shorthand for describing each and every value that is within the range. It should be appreciated and understood that the description in a range format is merely for convenience and brevity, and should not be construed as an inflexible limitation on the scope of any implementations or implementations disclosed herein. Accordingly, the disclosed range should be construed to have specifically disclosed all the possible subranges as well as individual numerical values within that range. As such, any value within the range may be selected as the terminus of the range. For example, description of a range such as from 1 to 5 should be considered to have specifically disclosed subranges such as from 1.5 to 3, from 1 to 4.5, from 2 to 5, from 3.1 to 5, etc., as well as individual numbers within that range, for example, 1, 2, 3, 3.2, 4, 5, etc. This applies regardless of the breadth of the range.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10° % (inclusive) of that numeral, or ±15% (inclusive) of that numeral. It should further be appreciated that when a numerical range is disclosed herein, any numerical value falling within the range is also specifically disclosed.

As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the composition, component, or phase.

All references cited herein are hereby incorporated by reference in their entireties. In the event of a conflict in a definition in the present disclosure and that of a cited reference, the present disclosure controls.

The present inventors have surprisingly and unexpectedly discovered that personal care compositions, such as emulsion-based personal care compositions, exhibit enhanced stability at an acidic pH (e.g., a pH of from about 4 to about 5) when an emulsifying system thereof includes glyceryl monostearate and polyoxyethylene (100) monostearate (PEG-100) stearate at substantially equal weight ratios (e.g., 0.9:1-1.1:1 or about 1:1), when the emulsifying system includes cetyl-stearyl alcohol and cetyl alcohol in a total amount of at least 3.5 weight %, based on a total weight of the personal care composition, and/or when the emulsifying system includes at least about 1.75 weight % of glyceryl monostearate and at least about 1.75 weight % of PEG-100 stearate. Particularly, the present inventors have surprisingly and unexpectedly discovered mineral oil-based or emulsion-based personal care compositions including an emulsifying system having a combination of glyceryl monostearate, PEG-100 stearate, cetyl alcohol, and cetyl-stearyl alcohol 50/50, exhibit relatively greater stability under various aging conditions and at an acidic pH of from about 4 to 5, when the emulsifying system includes glyceryl monostearate and PEG-100 stearate at substantially equal weight ratios of about 0.9:1 to about 1.1:1 or about 1:1, when the emulsifying system includes cetyl-stearyl alcohol and cetyl alcohol in a total amount of at least 3.5 weight %, based on a total weight of the personal care composition, and when the emulsifying system includes at least about 1.75 weight % of glyceryl monostearate and at least about 1.75 weight % of PEG-100 stearate.

Compositions

Compositions disclosed herein may be or include stable, emulsion-based personal care composition having an acidic pH. For example, the compositions disclosed herein may be or include a skin moisturizing composition, such as an emulsion-based skin moisturizing composition or emulsion-based lotion or cream having an acidic pH. The personal care compositions disclosed herein may exhibit enhanced or relatively greater stability as compared to conventional personal care compositions. For example, the personal care compositions disclosed herein may exhibit no phase separation, relatively stable pH, and/or relatively stable viscosity when exposed to various aging conditions. As further described herein, the personal care composition may include an emulsifying system including one or more surfactants and/or emulsifiers configured to provide enhanced or relatively greater stability to the personal care composition as compared to conventional personal care compositions.

The personal care composition may include a hydrophobic phase and a hydrophilic phase combined, mixed, contacted, or otherwise emulsified with one another. For example, the personal care composition may be a water-in-oil emulsion including a hydrophilic phase dispersed or suspended in a continuous hydrophobic phase. In another example, the personal care composition may be an oil-in-water emulsion including a hydrophobic phase dispersed or suspended in a continuous hydrophilic phase. In a preferred implementation, the personal care composition is an oil-in-water emulsion including a hydrophobic phase suspended in a continuous hydrophilic phase.

As discussed above, the personal care composition may have an acidic pH. For example, the personal care composition may have a pH of from about 3, about 3.5, about 4, or about 4.5 to about 5, about 5.5, about 6, or about 6.5. In another example, the personal care composition may have a pH of less than 7, less than 6.5, less than 6, less than 5.5, less than 5, or less than 4.5.

Hydrophilic Phase

The hydrophilic phase of the personal care composition may include water. Water of the hydrophilic phase may be deionized water, demineralized water, and/or softened water. In an exemplary implementation, the hydrophilic phase includes demineralized water and softened water. Water may make up the balance of the personal care composition. For example, the amount of water present in the personal care composition may be greater than 60 weight %, greater than 65 weight %, greater than 70 weight %, greater than 75 weight %, greater than 80 weight %, greater than 85 weight %, greater than 90 weight %, greater than 92 weight %, greater than 94 weight %, or greater than 96 weight %, based on a total weight of the personal care composition or the hydrophilic phase thereof. The amount of water in the personal care composition may include free water added and water introduced with other components or materials of the personal care composition. For example, the amount of the water in the personal care composition may include free water and water associated with one or more surfactants and/or any other components of the personal care composition.

In at least one implementation, hydrophilic phase may include one or more humectants. Illustrative humectants may be or include, but are not limited to, glycerin, propylene glycol, polyethylene glycol, ascorbic acid, ascorbyl dipalmitate, acetamide MEA, glucose glutamate, glucuronic acid, TEA-lactate, TEA-PCA, corn syrup, fructose, glucose, glycerin, glycol, 1,2,6-hexanetriol, sodium lactate, sodium PCA, hydrogenated starch hydrolysate, inositol, lactose, mannitol, PCA, PEG-10 propylene glycol, polyamino sugar condensate, propylene glycol, pyridoxine dilaurate, saccharide hydrolysate, hydroxystearyl methylglucamine, glucamine, maltitol, mannitol, methyl gluceth-10, methyl gluceth-20, riboflavin, PEG-4, PEG-6, PEG-8, PEG-9, PEG-10, PEG-12, PEG-14, PEG-16, PEG-18, PEG-20, PEG-32, PEG-40, glutamic acid, glycereth-7, glycereth-12, glycereth-26, saccharide isomerate, sorbeth-20, sorbitol, sucrose, thioglycerin, tris-(hydroxymethyl)nitromethane, tromethamine, histidine, PEG-75, PEG-135, PEG-150, PEG-200, PEG-5 pentaerythritol ether, polyglyceryl sorbitol, sorbitol, urea, xylitol, and the like, and combinations thereof. In a preferred implementation, the humectants may be or include, but is not limited to, propylene glycol.

The humectant may be present in an amount of from about 0.5 weight % to about 10 weight % or from about 0.5 weight % to about 20 weight %, based on a total weight of the personal care composition or the hydrophilic phase thereof. For example, the humectant (e.g., propylene glycol) may be present in an amount of from about 0.5 weight %, about 1 weight %, about 1.5 weight %, about 2 weight %, about 2.5 weight %, about 3 weight %, about 3.5 weight %, about 4 weight %, about 4.5 weight %, or about 5 weight % to about 5.5 weight %, about 6 weight %, about 6.5 weight %, about 7 weight %, about 7.5 weight %, about 8 weight %, about 8.5 weight %, about 9 weight %, about 9.5 weight %, about 10 weight %, or about 20 weight %, based on a total weight of the personal care composition or the hydrophilic phase thereof. In a preferred implementation, the humectant includes propylene glycol in an amount of from about 1.5 to about 6 weight %, about 3 weight % to about 5 weight %, about 3.5 weight % to about 4 weight %, or about 3.75 weight %, based on a total weight of the personal care composition or the hydrophilic phase thereof.

The hydrophilic phase may include one or more preservatives in an amount greater than 0 weight % and less than or equal to about 3 weight %, less than or equal to about 2.5 weight %, less than or equal to about 2 weight %, less than or equal to about 1.5 weight %, less than or equal to about 1 weight %, less than or equal to about 0.75 weight %, less than or equal to about 0.5 weight %, or less than or equal to about 0.25 weight %, based on a total weight of the personal care composition or the hydrophilic phase thereof. Illustrative preservatives may include, but are not limited to, caprylyl glycol, benzalkonium chloride; benzethonium chloride, 5-bromo-5-nitro-1,3-dioxane; 2-bromo-2-nitropropane-1,3-diol; alkyl trimethyl ammonium bromide; N-(hydroxymethyl)-N-(1,3-dihydroxy methyl-2,5-dioxo-4-imidaxolidinyl-N-(hydroxy methyl)urea; 1-3-dimethyol-5,5-dimethyl hydantoin; formaldehyde; iodopropynl butyl carbamate, butyl paraben; ethyl paraben; methyl paraben; propyl paraben, mixture of methyl isothiazolinone/methylchloroisothiazoline in a 1:3 wt. ratio; mixture of phenoxythanol/butyl paraben/methyl paraben/propylparaben; 2-phenoxyethanol; tris-hydroxyethyl-hexahydrotriazine; methylisothiazolinone; 5-chloro-2-methyl-4-isothiazolin-3-one; 1,2-dibromo-2,4-dicyanobutane; 1-(3-chloroalkyl)-3,5,7-triaza-azoniaadam-antane chloride; sodium benzoate; organic acids, sorbic acid, lactic acid, citric acid, and the like, and combinations thereof. In at least one implementation, the preservative includes sodium benzoate in an amount of from greater than 0 weight % to less than or equal to 2 weight %, greater than 0 weight % to less than or equal to 1 weight %, or about 0.5 weight %, based on a total weight of the personal care composition or the hydrophilic phase thereof. In another implementation, the preservative includes caprylyl glycol in an amount of from greater than 0 weight % to less than or equal to 2 weight %, greater than 0 weight % to less than or equal to 1 weight %, or about 0.3 weight %, based on a total weight of the personal care composition or the hydrophilic phase thereof. In yet another implementation, the preservative includes sodium benzoate and caprylyl glycol in an amount of from greater than 0 weight % to less than or equal to 2 weight %, greater than 0 weight % to less than or equal to 1 weight %, or greater than 0 weight % to less than or equal to 0.8 weight %, based on a total weight of the personal care composition or the hydrophilic phase thereof. For example, the hydrophilic phase may include caprylyl glycol in an amount of about 0.3 weight % and sodium benzoate in an amount of about 0.5 weight %, based on a total weight of the personal care composition or the hydrophilic phase thereof. In at least one implementation, the personal care compositions and/or the preservative system thereof may be free or substantially free of phenoxyethanol.

In at least one implementation, the hydrophilic phase may include one or more acids, one or more bases, and/or one or more buffers configured to adjust or control the pH of the personal care composition or the hydrophilic phase thereof. The one or more acids, one or more bases, and/or one or more buffers may, separately and independently, be present in an amount of from greater than 0 weight % to less than or equal to about 5 weight %, less than or equal to about 4 weight %, less than or equal to about 3 weight %, less than or equal to about 2 weight %, less than or equal to about 1 weight %, less than or equal to about 0.75 weight %, less than or equal to about 0.5 weight %, less than or equal to about 0.4 weight %, or less than or equal to about 0.35 weight %, based on a total weight of the personal care composition or the hydrophilic phase thereof. Illustrative bases may include, but are not limited to, ammonia; mono-, di-, and tri-alkyl amines; mono-, di-, and tri-alkanolamines; alkali metal and alkaline earth metal hydroxides; sodium hydroxide, potassium hydroxide, lithium hydroxide, monoethanolamine, triethylamine, isopropanolamine, diethanolamine, triethanolamine, and the like, and combinations thereof. Illustrative acids may include, but are not limited to, mineral acids, such as hydrochloric acid, nitric acid, phosphoic acid, and sulfuric acid, organic acids, polycarboxylic acids, such as citric acid, glycolic acid, and lactic acid, and the like, and combinations thereof. In a preferred implementation, the hydrophilic phase includes at least one acid, such as lactic acid, and the lactic acid is present in an amount of from greater than 0 weight % to about 0.5 weight %, or about 0.35 weight %, based on a total weight of the personal care composition or the hydrophilic phase thereof.

As further described herein, in at least one implementation, the personal care composition and the emulsifying system thereof may be free or substantially free of anionic surfactants, such as stearic acid, and the like. It should be appreciated that utilizing the anionic surfactant, stearic acid, as in conventional personal care compositions, may often require the neutralization of the stearic acid with a base, such as triethanolamine. As such, by providing a personal care composition that is free or substantially free of stearic acid, the personal care compositions disclosed herein may also be free or substantially free of triethanolamine. It should further be appreciated that conventional personal care compositions that include stearic acid and/or triethanolamine may not be capable of providing a pH of from about 4 to about 6 or about 4 to about 5, as the subsequent addition of an acid, such as lactic acid, results in precipitation or phase separation of the personal care composition. As such, the homogenous, stable personal care compositions and methods for preparing the personal care compositions disclosed herein, may be free or substantially free of steric acid and/or triethanolamine, and may further maintain a pH of from about 4 to about 6, or about 4 to about 5 (via the addition of one or more acids, such as lactic acid). Further, the stable personal care compositions disclosed herein may not exhibit any phase separation and/or precipitate formation (precipitation) after exposure to aging conditions.

Hydrophobic Phase

The hydrophobic phase of the personal care composition may include one or more acceptable or suitable carriers or hydrophobic liquids in an amount of from about greater than 0 weight % to less than or equal to about 5 weight %, about 1 weight % to about 4 weight %, about 2 weight % to about 3 weight %, or about 2.5 weight %, based on a total weight of the personal care composition or the hydrophobic phase thereof. Any suitable carriers or hydrophobic liquids that do not adversely affect the stability and/or efficacy of the personal care composition may be used. Illustrative hydrophobic liquids may include, but are not limited to, isopropyl myristate, mineral oil (e.g., white mineral oil, liquid paraffin, etc.), silicone oils (e.g., silicone 350 CS), or the like, or any combination thereof. Illustrative silicone oils may include, but are not limited to, chain polysiloxanes (e.g., dimethylpolysiloxane, methylphenyl polysiloxane, diphenyl polysiloxane, etc.), ring polysiloxanes (e.g., octamethylcyclotetrasiloxane, decamethyl cyclopenta siloxane, dodecamethyl cyclohexa siloxane, etc.), silicone resins forming a three-dimensional network structure, silicone rubbers, various modified polysiloxanes (e.g., amino-modified polysiloxane, polyether-modified polysiloxane, alkyl-modified polysiloxane, fluorine-modified polysiloxane, etc.), linear or branched organopolysiloxane, such as dimethylpolysiloxane, caprylyl methicone, phenyl trimethicone, tetrakis(trimethylsiloxy)silane, methylphenylpolysiloxane, methylhexylpolysiloxane, and dimethylsiloxane/methylphenylsiloxane copolymer; cyclic organopolysiloxanes such as octamethylcyclotetrasiloxane, decamethylcyclopentasiloxane, dodecamethylcyclohexasiloxane, tetramethyltetrahydrogencyclotetrasiloxane and tetramethyltetraphenylcyclotetrasiloxane; amino-modified organopolysiloxane, pyrrolidone-modified organopolysiloxane; silicone rubbers such as high-polymerized dimethylpolysiloxane rubber, amino-modified organopolysiloxane rubber, and dimethylsiloxane-methylphenylsiloxane-copolymer rubber; higher alkoxy-modified silicone such as stearoxy silicone, higher fatty acid-modified silicone, alkyl-modified silicone, long-chain alkyl-modified silicone, amino acid-modified silicone, fluorized silicone, and the like, and combinations thereof. In a preferred implementation, the hydrophobic phase of the personal care composition includes a combination of white mineral oil and silicone oil in an amount of from about 2 weight % to about 3 weight %, or about 2.5 weight %, based on a total weight of the personal care composition or the hydrophobic phase thereof.

The hydrophobic phase may include an emulsifying system including one or more surfactants and/or one or more emulsifiers configured to provide enhanced or relatively greater stability to the personal care composition, as compared to conventional personal care compositions. The one or more surfactants and/or emulsifiers may include one or more anionic surfactants, one or more cationic surfactants, one or more zwitterionic surfactants, one or more nonionic surfactants, and mixtures thereof.

Illustrative anionic surfactants may include, but are not limited to, stearic acid, water-soluble salts of higher fatty acid monoglyceride monosulfates, such as a sodium salt of a monosulfated monoglyceride of hydrogenated coconut oil fatty acids, such as sodium N-methyl N-cocoyl taurate, sodium cocomonoglyceride sulfate. Illustrative anionic surfactants may also include higher alkyl sulfates. As used herein, "higher alkyl" refers to $C_{6-30}$ alkyl. For example, the anionic surfactant may be or include sodium lauryl sulfate. The anionic surfactants may also include higher alkyl-ether sulfates. In another implementation, the anionic surfactant may include higher alkyl aryl sulfonates, such as sodium dodecyl benzene sulfonate (sodium lauryl benzene sulfonate), and higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. In an exemplary implementation, the anionic surfactant may be or include a water soluble salt of alkyl sulfates having from 10 to 18 carbon atoms in the alkyl radical and water soluble salts of sulfonated monoglycerides of fatty acids having from 10 to 18 carbon atoms. For example, the anionic surfactant may be or include, sodium lauryl sulfate, sodium lauroyl sarcosinate, sodium coconut monoglyceride sulfonates, or the like, and mixtures thereof.

In a preferred implementation, the personal care composition and the emulsifying system thereof may be free or substantially free of anionic surfactants. For example, the personal care composition and the emulsifying system thereof may be free or substantially free of stearic acid, and the like. As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the composition, component, or phase.

Illustrative nonionic surfactants may be or include, but are not limited to, higher alcohols or fatty alcohols, including straight chain alcohols or ethoxylates thereof, sorbitan fatty acid esters (e.g., sorbitan mono oleate, sorbitan mono isostearate, sorbitan mono laurate, sorbitan mono palmitate, sorbitan mono stearate, sorbitan sesquioleate, sorbitan trioleate, diglycerol sorbitan penta-2-ethylhexylate, diglycerol sorbitan tetra-2-ethylhexylate, etc.); glycerin polyglycerin aliphatic acids (e.g., mono cottonseed oil fatty acid glycerin, glyceryl monoerucate, glycerin sesquioleate, glyceryl monostearate, glyceryl stearate, α,α'-glycerin oleate pyroglutamate, monostearate glycerin malic acid, etc.); propylene glycol fatty acid esters (e.g., propylene glycol monostearatem, etc.); hydrogenated castor oil derivatives; glycerin alkylethers, and the like, and combinations thereof. Illustrative nonionic surfactants may also be or include, but are not limited to, sorbitan esters and ethoxylated sorbitan esters (e.g., PEG-20 sorbitan isostearate, sorbitan monolaurate, polysorbate-20, polysorbate-40, polysorbate-60, polysorbate-80); ethoxylates (e.g., Ceteth-20, PEG-30 castor oil, PEG-40 hydrogenated castor oil, PEG-60 hydrogenated castor oil, Laureth-7, Isolaureth-6, Steareth-10, Steareth-20, Steareth-21, Steareth-100, Ceteareth-12, Oleth-5, Oleth-10, etc.); ethoxylated adducts (e.g., PEG-25 stearate, glyceryl stearate, PEG-100 stearate, etc.); polyoxyethylene (100) monostearate, a polyethylene glycol ester of stearic acid, PEG esters (e.g., PEG-8 oleate, PEG-8 laurate, PEG-8 dilaurate, PEG-12 dilaurate, PEG-80 diisostearate, PEG-40 stearate, etc.); propoxylates (e.g., PPG-10 butanediol, PPG-50 oleyl ether, PPG-2-ceteareth-9, PPG-3-deceth-3, PPG-5-ceteth-20); ethoxylated modified triglycerides (e.g., PEG-20 corn glycerides, PEG-12 palm kernel glycerides); alkylphenol aromatic ethoxylates (e.g., dinonylphenol ethoxylate with 9 moles of EO octylphenol ethoxylate with 20 moles of EO, octylphenol ethoxylate with 40 moles of EO); block copolymers that are alkoxylated glycols having ethoxylated and propoxylated segments (e.g., POLOXAMER™ 182 and 234, POLOXAMER™ 105 Benzoate, and MEROXAPOL™ 174); and the like, and combinations thereof.

Illustrative fatty alcohols or higher alcohols may be or include, but are not limited to, straight chain alcohols, such as a $C_{12-22}$ fatty alcohol, or preferably a $C_{16-18}$ fatty alcohol, lauryl alcohol, myristyl alcohol, cetyl alcohol, behenyl alcohol, stearyl alcohol, cetyl-stearyl alcohol 50/50, and the like, and combinations thereof. Illustrative fatty alcohols may also include branch chain alcohols, such as monostearyl glycerin ether (batyl alcohol), 2-decyltetradecynol, lanolin alcohol, cholesterol, phytosterol, hexyl dodecanol, isostearyl alcohol, octyl dodecanol), and the like, and combinations thereof.

The amount of each of the one or more surfactants and/or emulsifiers present in the personal care composition or the emulsifying system thereof may vary widely. For example, each of the one or more surfactants and/or emulsifiers may, separately and independently, be present in an amount of from about greater than 0 weight % to less than or equal to about 10 weight %, based on a total weight of the personal care composition or the emulsifying system thereof. For example, each of the one or more surfactants and/or emulsifiers may, separately and independently, be present in an amount of from about greater than 0 weight %, about 0.5 weight %, about 1.5 weight %, about 2 weight %, about 2.5 weight %, or about 3 weight % to about 3.5 weight %, about 4 weight %, about 4.5 weight %, about 5 weight %, about 5.5 weight %, about 6 weight %, or greater, based on a total weight of the personal care composition or the emulsifying system thereof. In another example, each of the one or more surfactants and/or emulsifiers may, separately and independently, be present in an amount of from about greater than 0 weight %, about 1 weight %, about 2 weight %, about 3 weight %, about 4 weight %, or about 5 weight % to about 6 weight %, about 7 weight %, about 8 weight %, about 9 weight %, or about 10 weight %, based on a total weight of the personal care composition or the emulsifying system thereof.

In at least one implementation, each of the one or more surfactants and/or emulsifiers may, separately and independently, be present in an amount of less than or equal to 5 weight %, and greater than or equal to 1 weight %, greater than or equal to 1.5 weight %, greater than or equal to 1.75 weight %, greater than or equal to 2 weight %, greater than or equal to 2.25 weight %, greater than or equal to 2.5 weight %, greater than or equal to 2.75 weight %, greater than or equal to 3 weight %, greater than or equal to 3.5 weight %, or greater than or equal to 4 weight %, based on a total weight of the personal care composition or the emulsifying system thereof.

In another implementation, at least two of the one or more surfactants and/or emulsifiers may be present in an amount of greater than or equal to 1 weight %, greater than or equal to 1.5 weight %, greater than or equal to 1.75 weight %, greater than or equal to 2 weight %, greater than or equal to 2.25 weight %, greater than or equal to 2.5 weight %, greater than or equal to 2.75 weight %, greater than or equal to 3 weight %, greater than or equal to 3.5 weight %, greater than or equal to 4 weight %, greater than or equal to 4.25 weight %, greater than or equal to 4.5 weight %, greater than or equal to 5 weight c, greater than or equal to 5.5 weight %, greater than or equal to 6 weight %, greater than or equal to 6.5 weight %, greater than or equal to 7 weight %, greater than or equal to 7.5 weight %, and less than or equal to 15 weight %, based on a total weight of the personal care composition or the emulsifying system thereof.

In at least one implementation, a weight ratio of one surfactant or emulsifier to another surfactant or another emulsifier in the emulsifying system may vary from about 0.5:1 to about 1.5:1. For example, the weight ratio of any one surfactant/emulsifier to another surfactant/emulsifier in the emulsifying system may be from about 0.5:1, about 0.6:1, about 0.7:1, about 0.8:1, or about 0.9:1 to about 1:1, about 1.1:1, about 1.2:1, about 1.3:1, about 1.4:1, or about 1.5:1.

In a preferred implementation, the personal care composition and the emulsifying system thereof may include a combination of two or more nonionic surfactants and/or emulsifiers. For example, the personal care composition may include one or more fatty or higher alcohols and one or more nonionic surfactants. In another example, the personal care composition may include glyceryl monostearate or glyceryl stearate, PEG-100 stearate, cetyl alcohol, stearyl alcohol, cetyl-stearyl alcohol 50/50, and combinations thereof. In a preferred implementation, the personal care composition and the emulsifying system thereof may include a combination of glyceryl monostearate, PEG-100 stearate, cetyl alcohol, and cetyl-stearyl alcohol 50/50. In the preferred implementation, including the combination of glyceryl monostearate, PEG-100 stearate, cetyl alcohol, and cetyl-stearyl alcohol 50/50, the weight ratio of glyceryl monostearate to PEG-100 stearate may be from about 0.8:1 to about 1.2:1, about 0.9:1 to about 1.1:1, or about 1:1. For example, the amount of glyceryl monostearate and the amount of PEG-100 stearate may be substantially equal to one another. In the preferred implementation, including the combination of glyceryl monostearate, PEG-100 stearate, cetyl alcohol, and cetyl-stearyl alcohol 50/50, each of glyceryl monostearate and PEG-100 stearate may, separately and independently, be present in an amount of greater than or equal to about 1 weight %, greater than or equal to about 1.25 weight %, greater than or equal to about 1.5 weight %/0, greater than or equal to about 1.75 weight %, greater than or equal to about 2 weight %, or greater than or equal to about 2.25 weight %, and less than or equal to about 10 weight %, or less than or equal to about 6 weight %. In the preferred implementation, including the combination of glyceryl monostearate, PEG-100 stearate, cetyl alcohol, and cetyl-stearyl alcohol 50/50, a total amount of cetyl-stearyl alcohol 50/50 and cetyl alcohol combined may be greater than or equal to 2 weight %, greater than or equal to 2.25 weight %, greater than or equal to 2.5 weight %, greater than or equal to 2.75 weight %, greater than or equal to 3 weight %, greater than or equal to 3.5 weight %, greater than or equal to 4 weight %, greater than or equal to 4.25 weight %, greater than or equal to 4.5 weight %0, greater than or equal to 5 weight %, or greater than or equal to 5.5 weight %, and less than or equal to about 10 weight %. In a preferred implementation, the total amount of cetyl-stearyl alcohol 50/50 and cetyl alcohol combined is greater than 3.5 weight % and less than or equal to about 6 weight %, based on a total weight of the personal care composition or the emulsifying system thereof.

Skin Care Agents

In some implementation, the personal care composition may include one or more skin care agents. Any suitable skin care agents that do not adversely affect the stability and/or efficacy of the personal care composition may be used. In at least one implementation, the skin care agent may include one or more emollients configured to maintain a soft, smooth, and pliable appearance to the skin. As is known by those skilled in the art, the emollients may function by remaining on the surface of the skin or in the stratum corneum to act as a lubricant, to reduce flaking, and/or to improve the appearance of the skin.

The skin care agents may generally include one or more polymers (e.g., polyvinylpyrrolidine), starches (e.g., tapioca starches, hydrophobically modified corn starch, such as DRY-FLO TS® CAS Nos. 68989-12-8, 68554-70-1, 9005-25-8, etc.), protein derivatives (e.g., derivatized hydrolyzed wheat protein), ethoxylated fatty ethers, cellulosics (e.g., hydroxyethylcellulose), and the like, and combinations thereof. Illustrative skin care agents may include, but are not limited to, esters comprising an aliphatic alcohol having about 2 to about 18 carbon atoms condensed with an aliphatic or aromatic carboxylic acid including about 8 to about 20 carbon atoms (e.g., isopropyl myristate, decyl oleate, cetearyl isononanate, etc.). The esters may be straight chained or branched. In a preferred implementation, the ester has a molecular weight of less than about 500.

Other skin care agents may include, but are not limited to, polyvinyl-pyrrolidone, polyquaternium-4, polyquaternium-7, polyquaternium-10, guar gum derivatives, hydroxypropylmethylcellulose, hydroxyethylcellulose, a polyethylene glycol, a methyl ether of a polyethylene glycol, quaternium-79, wheat germamidopropyl hydroxypropyl dimonium hydrolyzed wheat protein, stearyl methicone, dimethicone copolyol, dimethicone propyl PG betaine, poly(sodium styrene sulfonate), sorbitan oleate, steareth-2, steareth-21, isoceteth-20, PEG-7 glyceryl cocoate, PEG-75 lanolin, glycereth-26, PPG-5-ceteth-20, a $C_{12}$-$C_{20}$ alcohol, canola oil, glyceryl laurate, triglyceryl monostearate, glyceryl monostearate, vitamin E acetate, sunflower seed amidopropylethyldimonium ethylsulfate, sodium PEG-7 olive oil carboxylate, PPG-1 hydroxyethyl caprylamide, PPG-2 hydroxyethyl cocamide, mineral oil, petrolatum, aloe barbadensis, isostearamidopropylmorpholine lactate, strontium acetate, palmitamidopropyltrimonium chloride, and the like, and combinations thereof. In a preferred implementation, the skin care agent is or includes a conditioner, such as a cationic cellulose polymer (e.g., polyquaternium-7).

Additional Optional Components/Ingredients

The personal care composition may include one or more additional optional ingredients. Illustrative optional ingredients may include, but are not limited to, one or more dyes, fragrances, buffers, and buffering agents (e.g., inorganic phosphates, sulfates, and carbonates), preservatives (e.g., parabens, etc.), thickeners, viscosity modifiers, antioxidants, foam enhancers, chelating agents (e.g., EDTA, phosphates, etc.), opacifiers, hydric solvents, hydrotropes, antimicrobials, and the like, and combinations thereof. In at least one implementation, the personal care compositions disclosed herein may be free or substantially free of ethylenediaminetetraacetic acid (EDTA) and/or one or more carbomers.

Methods

The present disclosure may provide methods for preparing stable personal care compositions having an acidic pH. The present disclosure may also provide methods for preventing the separation of hydrophobic and hydrophilic phases in personal care compositions when exposed to aging conditions (e.g., heating at 25° C., 40° C., and 49° C., cooling at 4° C., freeze/thaw, exposure to sun, etc.). The method may include preparing a hydrophobic phase and a hydrophilic phase, and contacting the hydrophobic phase with the hydrophilic phase. For example, the method may include preparing the hydrophobic phase including one or more of the components disclosed herein, preparing the hydrophobic phase including one or more of the components disclosed herein, and mixing, combining, stirring, emulsifying, or otherwise contacting the hydrophobic phase and the hydrophilic phase with one another. The method may also include preparing an emulsifying system including one or more surfactants and/or emulsifiers to enhance the stability of the personal care composition. The method of preparing the emulsifying system may include mixing, combining, stirring, or otherwise contacting the one or more surfactants and/or emulsifiers with one another. For example, the method of preparing the emulsifying system may include mixing, combining, stirring, or otherwise contacting glyceryl monostearate, PEG-100 stearate, cetyl alcohol, and cetyl-stearyl alcohol 50/50 with one another. The weight ratio of glyceryl monostearate to PEG-100 stearate may be from about 0.8:1 to about 1.2:1, about 0.9:1 to about 1.1:1, or about 1:1. Each of glyceryl monostearate and PEG-100 stearate may, separately and independently, be present in an amount of greater than or equal to about 1 weight %, greater than or equal to about 1.25 weight %, greater than or equal to about 1.5 weight %, greater than or equal to about 1.75 weight %, greater than or equal to about 2 weight %, or greater than or equal to about 2.25 weight %, and less than or equal to about 10 weight %, or less than or equal to about 6 weight %. The total amount of cetyl-stearyl alcohol 50/50 and cetyl alcohol combined may be greater than or equal to 2 weight %, greater than or equal to 2.25 weight %, greater than or equal to 2.5 weight %, greater than or equal to 2.75 weight %, greater than or equal to 3 weight %, greater than or equal to 3.5 weight %, greater than or equal to 4 weight %, greater than or equal to 4.25 weight %, greater than or equal to 4.5 weight %, greater than or equal to 5 weight %, or greater than or equal to 5.5 weight %, and less than or equal to about 10 weight %.

All ingredients for use in the compositions described herein should be topically acceptable. As used herein, "topically acceptable" may refer any ingredient that is present in a composition as described in an amount and form which does not render the composition unsafe for use on surfaces of skin.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

Personal care compositions (1)-(17), namely emulsion-based skin moisturizing compositions, were prepared by combining the ingredients/components according to Tables 1A and 1B. Particularly, respective hydrophilic or water phases and hydrophobic or oil phases of each of the personal care compositions (1)-(17) were prepared separately by combining the components according to Table 1A and 1B, the respective hydrophilic phases were then combined with the respective hydrophobic phases at a temperature of about 70° C. to about 75° C., homogenized or emulsified for about 10 minutes (min), and cooled to room temperature (RT) under mixing.

Example 2

The stability of each of the personal care compositions (1)-(17) prepared in Example 1 was evaluated. Particularly, the stability of each of the personal care compositions (1)-(17) of Example 1 was evaluated by observing the changes in pH, changes in viscosity, and separation of phases via visual inspection. Each of the samples was placed

TABLE 1A

Personal Care Compositions (1)-(8) Weight (%)

| COMPONENT | 1 | 2 | 3 | 4 | 5 | 6 | 7 | 8 |
|---|---|---|---|---|---|---|---|---|
| HYDROPHILIC PHASE | | | | | | | | |
| Water | * | * | * | * | * | * | * | * |
| Propylene Glycol | 1.5 | 6 | 6 | 3.75 | 6 | 6 | 1.5 | 6 |
| Sodium Benzoate | 0.5 | 0.5 | 0.5 | 0.5 | 0.5 | 0.5 | 0.5 | 0.5 |
| Lactic Acid | 0.35 | 0.35 | 0.35 | 0.35 | 0.35 | 0.35 | 0.35 | 0.35 |
| Caprylyl Glycol | 0.3 | 0.3 | 0.3 | 0.3 | 0.3 | 0.3 | 0.3 | 0.3 |
| HYDROPHOBIC PHASE | | | | | | | | |
| White Mineral Oil | 2 | 2 | 2 | 2 | 2 | 2 | 2 | 2 |
| Glyceryl Monostearate | 0.5 | 0.5 | 0.5 | 1.75 | 3 | 3 | 0.5 | 3 |
| Cetyl-Stearyl Alcohol 50/50 | 3 | 3 | 0.5 | 1.75 | 3 | 0.5 | 3 | 0.5 |
| Silicone Oil (polydimethylsiloxane) (PDMS) 350 CS | 0.5 | 0.5 | 0.5 | 0.5 | 0.5 | 0.5 | 0.5 | 0.5 |
| PEG-100 Stearate | 3 | 3 | 0.5 | 1.75 | 0.5 | 3 | 0.5 | 0.5 |
| Cetyl Alcohol | 3 | 0.5 | 0.5 | 1.75 | 0.5 | 0.5 | 0.5 | 3 |
| Total | 100 | 100 | 100 | 100 | 100 | 100 | 100 | 100 |
| Total Cetyl-Stearyl Alcohol and Cetyl Alcohol | 6 | 3.5 | 1 | 3.5 | 3.5 | 1 | 3.5 | 3.5 |

* Water made up the balance of the hydrophilic phase of the personal care compositions

TABLE 1B

Personal Care Compositions (9)-(17)

| COMPONENT | 9 | 10 | 11 | 12 | 13 | 14 | 15 | 16 | 17 |
|---|---|---|---|---|---|---|---|---|---|
| HYDROPHILIC PHASE | | | | | | | | | |
| Water | * | * | * | * | * | * | * | * | * |
| Propylene Glycol | 1.5 | 6 | 6 | 1.5 | 1.5 | 6 | 1.5 | 1.5 | 1.5 |
| Sodium Benzoate | 0.5 | 0.5 | 0.5 | 0.5 | 0.5 | 0.5 | 0.5 | 0.5 | 0.5 |
| Lactic Acid | 0.35 | 0.35 | 0.35 | 0.35 | 0.35 | 0.35 | 0.35 | 0.35 | 0.35 |
| Caprylyl Glycol | 0.3 | 0.3 | 0.3 | 0.3 | 0.3 | 0.3 | 0.3 | 0.3 | 0.3 |
| HYDROPHOBIC PHASE | | | | | | | | | |
| White Mineral Oil | 2 | 2 | 2 | 2 | 2 | 2 | 2 | 2 | 2 |
| Glyceryl Monostearate | 0.5 | 0.5 | 3 | 0.5 | 3 | 0.5 | 3 | 3 | 3 |
| Cetyl-Stearyl Alcohol 50/50 | 0.5 | 0.5 | 3 | 0.5 | 3 | 3 | 0.5 | 0.5 | 3 |
| Silicone 350 CS | 0.5 | 0.5 | 0.5 | 0.5 | 0.5 | 0.5 | 0.5 | 0.5 | 0.5 |
| PEG-100 Stearate | 3 | 3 | 3 | 0.5 | 0.5 | 0.5 | 3 | 0.5 | 3 |
| Cetyl Alcohol | 0.5 | 3 | 3 | 3 | 3 | 3 | 3 | 0.5 | 0.5 |
| Total | 100 | 100 | 100 | 100 | 100 | 100 | 100 | 100 | 100 |
| Total Cetyl-Stearyl Alcohol and Cetyl Alcohol | 1 | 3.5 | 6 | 3.5 | 6 | 6 | 3.5 | 1 | 3.5 |

* Water made up the balance of the hydrophilic phase of the personal care compositions in a respective 4 oz. glass jar and placed in an oven at the temperature and time indicated in Tables 2-5. After the respective times of each of the studies elapsed, each of the samples was removed from the oven and allowed to cool for about 24 hours in a monitored stability chamber maintained at about 25° C. After cooling to about 25° C., the viscosity and pH were measured, and the samples were observed visually for any phase separation. Viscosity was measured using a Brookfield rheometer with spindle T-E at 5 RPM for about 1 minute. The stability, as indicated by pH and viscosity, under the varying temperature conditions is summarized in Tables 2-5.

TABLE 2A pH of Personal Care Compositions (1)-(17) at 25° C.

| Sample | 0 weeks | 4 weeks | 8 weeks | 13 weeks |
|---|---|---|---|---|
| 1 | 4.47 | 4.16 | 4.31 | 4.39 |
| 2 | 4.49 | 4.25 | 4.39 | 4.42 |
| 3 | Separated | Separated | Separated | Separated |
| 4 | 4.4 | 4.15 | 4.33 | 4.32 |
| 5 | 4.4 | 4.3 | 4.28 | 4.28 |
| 6 | 4.46 | 4.3 | 4.27 | 4.34 |
| 7 | Separated | Separated | Separated | Separated |
| 8 | 4.39 | 4.2 | 4.28 | 4.34 |
| 9 | 4.33 | 4.23 | Separated | Separated |
| 10 | 4.33 | 4.24 | 4.28 | 4.44 |
| 11 | 4.5 | 4.28 | 4.38 | 4.41 |
| 12 | Separated | Separated | Separated | Separated |
| 13 | 4.45 | 4.13 | 4.23 | 4.31 |
| 14 | Separated | Separated | Separated | Separated |
| 15 | 4.42 | 4.18 | 4.27 | 4.34 |
| 16 | 4.31 | 4.16 | 4.18 | Separated |
| 17 | 4.47 | 4.2 | 4.29 | 4.31 |

TABLE 2B

Viscosity (TE) of Personal Care Compositions (1)-(17) at 25° C.

| Sample | 0 weeks | 4 weeks | 8 weeks | 13 weeks |
|---|---|---|---|---|
| 1 | 42,000 | 57,000 | 45,000 | 46,000 |
| 2 | 68,000 | 71,000 | 66,000 | 60,000 |
| 3 | Separated | Separated | Separated | Separated |
| 4 | 85,000 | 122,000 | 114,000 | 114,000 |
| 5 | 24,000 | 127,000 | 47,000 | 163,000 |
| 6 | 3,000 | 8,000 | 12,000 | 11,000 |
| 7 | Separated | Separated | Separated | Separated |
| 8 | 38,000 | 166,000 | 168,000 | 162,000 |
| 9 | 2,000 | 8,000 | Separated | Separated |
| 10 | 63,000 | 61,000 | 48,000 | 55,000 |
| 11 | 154,000 | 220,000 | 201,000 | 188,000 |
| 12 | Separated | Separated | Separated | Separated |
| 13 | 62,000 | 176,000 | 180,000 | 184,000 |
| 14 | Separated | Separated | Separated | Separated |
| 15 | 85,000 | 90,000 | 106,000 | 102,000 |
| 16 | 15,000 | 18,000 | 37,000 | Separated |
| 17 | 153,000 | 120,000 | 115,000 | 109,000 |

TABLE 3A pH of Personal Care Compositions (1)-(17) at 40° C.

| Sample | 0 weeks* | 4 weeks | 8 weeks | 13 weeks |
|---|---|---|---|---|
| 1 | 4.47 | 4.29 | 4.34 | 4.31 |
| 2 | 4.49 | 4.21 | 4.2 | 4.33 |
| 3 | Separated | Separated | Separated | Separated |
| 4 | 4.4 | 4.29 | 4.26 | 4.28 |
| 5 | 4.4 | 4.22 | 4.18 | 4.25 |
| 6 | 4.46 | 4.30 | 4.24 | 4.25 |
| 7 | Separated | Separated | Separated | Separated |
| 8 | 4.39 | 4.23 | 4.21 | 4.28 |
| 9 | 4.33 | Separated | Separated | Separated |
| 10 | 4.33 | 4.27 | 4.2 | 4.43 |
| 11 | 4.5 | 4.3 | 4.37 | 4.38 |
| 12 | Separated | Separated | Separated | Separated |
| 13 | 4.45 | 4.2 | 4.39 | 4.33 |
| 14 | Separated | Separated | Separated | Separated |
| 15 | 4.42 | 4.26 | 4.29 | 4.32 |
| 16 | 4.31 | Separated | 4.21 | Separated |
| 17 | 4.47 | 4.35 | 4.24 | 4.31 |

*Initial measurement at Time = 0 was taken at 25° C.

TABLE 3B

Viscosity (TE) of Personal Care Compositions (1)-(17) at 40° C.

| Sample | 0 weeks* | 4 weeks | 8 weeks | 13 weeks |
|---|---|---|---|---|
| 1 | 42,000 | 53,000 | 58,000 | 61,000 |
| 2 | 68,000 | 53,000 | 65,000 | 70,000 |
| 3 | Separated | Separated | Separated | Separated |
| 4 | 85,000 | 104,000 | 103,000 | 122,000 |
| 5 | 24,000 | 45,000 | 118,000 | 60,000 |
| 6 | 3,000 | 8,000 | 23,000 | 24,000 |
| 7 | Separated | Separated | Separated | Separated |
| 8 | 38,000 | 61,000 | 52,000 | 77,000 |
| 9 | 2,000 | Separated | Separated | Separated |
| 10 | 63,000 | 65,000 | 68,000 | 56,000 |
| 11 | 154,000 | 237,000 | 188,000 | 172,000 |
| 12 | Separated | Separated | Separated | Separated |
| 13 | 62,000 | 74,000 | 85,000 | 105,000 |
| 14 | Separated | Separated | Separated | Separated |
| 15 | 85,000 | 135,000 | 104,000 | 119,000 |
| 16 | 15,000 | Separated | 53,000 | Separated |
| 17 | 153,000 | 139,000 | 134,000 | 157,000 |

*Initial measurement at Time = 0 was taken at 25° C.

TABLE 4A pH of Personal Care Compositions (1)-(17) at 49° C.

| Sample | 0 weeks* | 4 weeks |
|---|---|---|
| 1 | 4.47 | Separated |
| 2 | 4.49 | Separated |
| 3 | Separated | Separated |
| 4 | 4.4 | 4.21 |
| 5 | 4.4 | Separated |
| 6 | 4.46 | Separated |
| 7 | Separated | Separated |
| 8 | 4.39 | Separated |
| 9 | 4.33 | Separated |
| 10 | 4.33 | Separated |
| 11 | 4.5 | 4.29 |
| 12 | Separated | Separated |
| 13 | 4.45 | Separated |
| 14 | Separated | Separated |
| 15 | 4.42 | 4.22 |

TABLE 4A-continued pH of Personal Care Compositions (1)-(17) at 49° C.

| Sample | Time | |
|---|---|---|
| | 0 weeks* | 4 weeks |
| 16 | 4.31 | Separated |
| 17 | 4.47 | 4.09 |

*Initial measurement at Time = 0 was taken at 25° C.

TABLE 4B

Viscosity (TE) of Personal Care Compositions (1)-(17) at 49° C.

| Sample | Time | |
|---|---|---|
| | 0 weeks* | 4 weeks |
| 1 | 42,000 | Separated |
| 2 | 68,000 | Separated |
| 3 | Separated | Separated |
| 4 | 85,000 | 64,000 |
| 5 | 24,000 | Separated |
| 6 | 3,000 | Separated |
| 7 | Separated | Separated |
| 8 | 38,000 | Separated |
| 9 | 2,000 | Separated |
| 10 | 63,000 | Separated |
| 11 | 154,000 | 141,000 |
| 12 | Separated | Separated |
| 13 | 62,000 | Separated |
| 14 | Separated | Separated |
| 15 | 85,000 | 93,000 |
| 16 | 15,000 | Separated |
| 17 | 153,000 | 111,000 |

*Initial measurement at Time = 0 was taken at 25° C.

TABLE 5A pH of Personal Care Compositions (1)-(17) at 4° C.

| Sample | Time | | | |
|---|---|---|---|---|
| | 0 weeks* | 4 weeks | 8 weeks | 13 weeks |
| 1 | 4.47 | 4.23 | 4.34 | 4.42 |
| 2 | 4.49 | 4.25 | 4.39 | 4.41 |
| 3 | Separated | Separated | Separated | Separated |
| 4 | 4.4 | 4.27 | 4.34 | 4.34 |
| 5 | 4.4 | 4.24 | 4.34 | 4.26 |
| 6 | 4.46 | 4.25 | 4.28 | 4.32 |
| 7 | Separated | Separated | Separated | Separated |
| 8 | 4.39 | 4.31 | 4.26 | 4.33 |
| 9 | 4.33 | 4.2 | Separated | Separated |
| 10 | 4.33 | 4.3 | 4.4 | 4.4 |
| 11 | 4.5 | 4.28 | 4.41 | 4.38 |
| 12 | Separated | Separated | Separated | Separated |
| 13 | 4.45 | 4.15 | 4.33 | 4.27 |
| 14 | Separated | Separated | Separated | Separated |
| 15 | 4.42 | 4.24 | 4.34 | 4.33 |
| 16 | 4.31 | 4.14 | 4.21 | Separated |
| 17 | 4.47 | 4.15 | 4.34 | 4.32 |

*Initial measurement at Time = 0 was taken at 25° C.

TABLE 5B

Viscosity (TE) of Personal Care Compositions (1)-(17) at 4° C.

| Sample | Time | | | |
|---|---|---|---|---|
| | 0 weeks* | 4 weeks | 8 weeks | 13 weeks |
| 1 | 42,000 | 94,000 | 101,000 | 97,000 |
| 2 | 68,000 | 42,000 | 43,000 | 34,000 |
| 3 | Separated | Separated | Separated | Separated |
| 4 | 85,000 | 83,000 | 77,000 | 75,000 |
| 5 | 24,000 | 86,000 | 88,000 | 86,000 |
| 6 | 3,000 | 6,000 | 9,000 | 6,000 |
| 7 | Separated | Separated | Separated | Separated |
| 8 | 38,000 | 107,000 | 191,000 | 183,000 |
| 9 | 2,000 | 8000 | Separated | Separated |
| 10 | 63,000 | 6000 | 9,000 | 2,000 |
| 11 | 154,000 | 156000 | 163,000 | 136,000 |
| 12 | Separated | Separated | Separated | Separated |
| 13 | 62,000 | 274,000 | 351,000 | 369,000 |
| 14 | Separated | Separated | Separated | Separated |
| 15 | 85,000 | 91,000 | 78,000 | 85,000 |
| 16 | 15,000 | 25,000 | 28,000 | Separated |
| 17 | 153,000 | 135,000 | 100,000 | 131,000 |

*Initial measurement at Time = 0 was taken at 25° C.

Example 3

The stability of each of the personal care compositions (1)-(17) prepared in Example 1 was evaluated by varying freeze/thaw conditions. To evaluate the stability under freeze/thaw conditions, each of the personal care compositions (1)-(17) was placed in respective 4 oz. glass jars and subsequently placed in a container maintained at either −30° C. or −10° C. The freeze/thaw condition was a rapid treatment. Particularly, each of the samples was left in the cooled containers for about three days. After cooling for about three days, each of the samples was removed and immediately placed in the monitored stability chamber maintained at about 25° C. for about 24 hours. This process was repeated for a total of three cycles. Each of the personal care compositions (1)-(17) was further evaluated under both a slow freeze-thaw conditions at −30° C. For the slow freeze-thaw conditions at −30° C., each of the personal care compositions (1)-(17) was placed in the −30° C. cooled container for about two days, then placed in a −10° C. cooled container for two days, and then placed in a 4° C. cooled container for two days. After the six cooling treatment under −30° C., −10° C., and 4° C., each of the personal care compositions (1)-(17) was placed the monitored stability chamber maintained at about 25° C. for about two days, and subsequently evaluated. The stability of each of the personal care compositions (1)-(17) under the varying freeze/thaw conditions is summarized in Tables 6A and 6B.

TABLE 6A pH Measured for Rapid Freeze/Thaw Conditions of Personal Care Compositions (1)-(17)

| Sample | Time | | |
|---|---|---|---|
| | Slow/−30° C. | Rapid/−30° C. | Rapid/−10° C. |
| 1 | 4.18 | 4.18 | 4.35 |
| 2 | 4.23 | 4.17 | 4.35 |
| 3 | Separated | Separated | Separated |
| 4 | 4.17 | 4.18 | 4.2 |
| 5 | 4.23 | 4.25 | 4.18 |
| 6 | 4.23 | 4.31 | 4.25 |
| 7 | Separated | Separated | Separated |

TABLE 6A-continued pH Measured for Rapid Freeze/Thaw Conditions of Personal Care Compositions (1)-(17)

| Sample | Time Slow/−30° C. | Rapid/−30° C. | Rapid/−10° C. |
|---|---|---|---|
| 8 | 4.26 | 4.15 | 4.27 |
| 9 | 4.2 | 4.19 | Separated |
| 10 | 4.28 | 4.32 | 4.27 |
| 11 | 4.25 | 4.29 | 4.19 |
| 12 | Separated | Separated | Separated |
| 13 | 4.17 | 4.26 | 4.26 |
| 14 | Separated | Separated | Separated |
| 15 | 4.26 | 4.26 | 4.19 |
| 16 | 4.15 | 4.12 | 4.21 |
| 17 | 4.27 | 4.2 | 4.24 |

TABLE 6B

Viscosity (TE) Measured for Rapid Freeze/Thaw Conditions of Personal Care Compositions (1)-(17)

| Sample | Time Slow/−30° C. | Rapid/−30° C. | −10° C. |
|---|---|---|---|
| 1 | 113,000 | 108,000 | 125,000 |
| 2 | 57,000 | 41,000 | 55,000 |
| 3 | Separated | Separated | Separated |
| 4 | 150,000 | 87,000 | 177,000 |
| 5 | 114,000 | 100,000 | 123,000 |
| 6 | 15,000 | 13,000 | 10,000 |
| 7 | Separated | Separated | Separated |
| 8 | 116,000 | 56,000 | 104,000 |
| 9 | 7,000 | 6,000 | Separated |
| 10 | 6,000 | 9,000 | 6,000 |
| 11 | 184,000 | 108,000 | 163,000 |
| 12 | Separated | Separated | Separated |
| 13 | 177000 | 180,000 | 189,000 |
| 14 | Separated | Separated | Separated |
| 15 | 163,000 | 100,000 | 118,000 |
| 16 | 85,000 | 93,000 | 117,000 |
| 17 | 114,000 | 100,000 | 105,000 |

Example 4

The stability of each of the personal care compositions (1)-(17) prepared in Example 1 was evaluated under exposure to the sun. Particularly, each of the personal care compositions (1)-(17) was placed in respective 4 oz. glass jars and subsequently placed in a window exposed to the sun for about four weeks. After four weeks, each of the samples was removed and placed in the monitored stability chamber maintained at about 25° C. for about 24 hours, and the pH and viscosity was measured as discussed above. The stability of each of the personal care compositions (1)-(17) when exposed to the sun is summarized in Table 7.

TABLE 7

Viscosity (TE) and pH Measured for Personal Care Compositions (1)-(17) Exposed to Sun for Four Weeks

| Sample | Time pH | Viscosity (TE) |
|---|---|---|
| 1 | 4.31 | 47,000 |
| 2 | 4.31 | 89,000 |
| 3 | Separated | Separated |
| 4 | 4.33 | 103,000 |
| 5 | 4.25 | 186,000 |
| 6 | 4.32 | 45,000 |
| 7 | Separated | Separated |
| 8 | 4.30 | 214,000 |
| 9 | 4.28 | 15,000 |
| 10 | 4.4 | 77,000 |
| 11 | 4.36 | 192,000 |
| 12 | Separated | Separated |
| 13 | 4.28 | 116,000 |
| 14 | Separated | Separated |
| 15 | 4.31 | 152,000 |
| 16 | 4.2 | 60,000 |
| 17 | 4.23 | 178,000 |

As illustrated in Examples 2-4 and Tables 2-7, it was surprisingly and unexpectedly discovered that emulsion-based personal care compositions or emulsion-based skin moisturizing compositions (1)-(17) having a pH from about 4 to about 5, maintain stability at varying conditions when glyceryl monostearate and PEG-100 stearate are included in substantially equal amounts and when a total amount of cetyl-stearyl alcohol and cetyl alcohol is included in an amount of at least 3.5 weight %. For example, each of the personal care compositions (4), (11), (15), and (17) did not exhibit any separation and maintained relatively stable pH and viscosity profiles throughout the various aging conditions. The stability was further observed in the extreme heating conditions when heating to a temperature of about 49° C. for four weeks. It was further observed that each of the personal care compositions (4), (11), (15), and (17) maintained their color, odor, and appearance throughout the various testing conditions.

As further illustrated in Examples 2-4 and Tables 2-7, each of the personal care compositions (3), (6), (7), (12), and (14) included about equal amounts of glyceryl monostearate and PEG-100 stearate, but these were not stable in all the aging conditions. For example, each of the personal care compositions (3), (7), (12), and (14) exhibited separation within about 24 hours at about 25° C., and personal care composition (6) exhibited separation at about 49° C. in less than four weeks. Personal care composition (3) included glyceryl monostearate and PEG-100 stearate in equal amounts, but only a combined total of cetyl-steryl alcohol and cetyl alcohol of about 1 weight %. Similarly, personal care composition (6) included substantially equal amounts of glyceryl monostearate and PEG-100 stearate, but only a combined total of cetyl-steryl alcohol and cetyl alcohol of about 1 weight %. Personal care composition (7) included substantially equal amounts of glyceryl monostearate and PEG-100 stearate at about 0.5%, and a combined total of cetyl-steryl alcohol and cetyl alcohol of about 3.5 weight %. Both personal care compositions (12) and (14) included substantially equal amounts of glyceryl monostearate and PEG-100 stearate at about 0.5%, and a combined total of cetyl-steryl alcohol and cetyl alcohol of about 3.5 weight % and 6 weight %, respectively.

As further illustrated in Examples 2-4 and Tables 2-7, each of the personal care compositions (1), (2), (5), (8)-(10), and (13) exhibited separation in less than four weeks when maintained at about 49° C. Further, personal care composition (16) exhibited separation at about 49° C., about 25° C., and about 40° C. None of (1), (2), (5), (8)-(10), (13), and (16) included glyceryl monostearate and PEG-100 stearate at equal amounts.

Based on the evaluation of each of the personal care compostions (1)-(17), it was surprisingly and unexpectedly discovered that stable personal care compositions are prepared by including each of glyceryl monostearate and PEG-100 stearate in an amount of at least about 1.5 weight %. For example, stable personal care compositions may be prepared by including at least about 1.75 weight % of glyceryl monostearate and at least about 1.75 weight % of PEG-100 stearate. Further, as discussed above, it was further surprisingly and unexpectedly discovered that stable personal care compositions are prepared by including cetyl-stearyl alcohol and cetyl alcohol in a total amount of at least about 3.5 weight %.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

The invention claimed is:

1. A personal care composition, comprising an emulsion of a hydrophobic phase and a hydrophilic phase,
    wherein the hydrophobic phase comprises an emulsifying system comprising a first nonionic surfactant and a second nonionic surfactant,
    wherein a weight ratio of the first nonionic surfactant to the second nonionic surfactant is from about 0.9:1 to about 1.1:1,
    wherein the first nonionic surfactant is glyceryl monostearate,
    wherein the second nonionic surfactant is PEG-100 stearate,
    wherein the glyceryl monostearate and the PEG-100 stearate are each, independently and separately, present in an amount of from about 1.75 weight % to about 6 weight %, based on a total weight of the personal care composition,
    wherein the emulsifying system further comprises cetyl alcohol and cetylstearyl alcohol 50/50 which are present in a total amount of from about 3.5 weight % to about 6 weight %, based on a total weight of the personal care composition,
    wherein the hydrophobic phase further comprises a hydrophobic liquid carrier comprising mineral oil and silicone oil;
    wherein the hydrophilic phase comprises water;
    wherein the hydrophilic phase further comprises propylene glycol in an amount of from about 1.5 weight % to about 6 weight %, based on a total weight of the personal case composition;
    wherein the hydrophilic phase further comprises one or more preservatives, and wherein the preservatives comprise sodium benzoate and caprylyl glycol,
    wherein the hydrophilic phase further comprises one or more one or more acids, and wherein the one or more acids comprise lactic acid, and
    wherein the personal care composition has a pH of from about 4 to about 6.

2. The personal care composition of claim 1, wherein the glyceryl monostearate and the PEG-100 stearate are each, independently and separately, present in an amount of from 1.75 weight % to 3 weight %, based on a total weight of the personal care composition.

3. The personal care composition of claim 1, wherein the term "about" in conjunction with a numeral refers to a value that is ±15% (inclusive) of that numeral.

4. The personal care composition of claim 1, wherein the personal care composition has a pH of from about 4 to about 5.

5. The personal care composition of claim 1, wherein the hydrophobic liquid carrier comprises white mineral oil and silicone oil in an amount of from 2 weight % to 3 weight %, based on a total weight of the personal care composition.

6. The personal care composition of claim 1, wherein the term "about" in conjunction with a numeral refers to a value that is ±10% (inclusive) of that numeral.

7. The personal care composition of claim 1, wherein the sodium benzoate is present in an amount of about 0.5 weight % and the caprylyl glycol is present in an amount of about 0.3 weight %, based on a total weight of the personal care composition.

8. The personal care composition of claim 1, wherein the lactic acid is present in an amount of about 0.35 weight %, based on a total weight of the personal care composition.

9. The personal care composition of claim 1, wherein the personal care composition is free of stearic acid.

10. The personal care composition of claim 1, wherein the personal care composition is free of anionic surfactants.

11. A method for preparing the personal care composition of claim 1, the method comprising emulsifying the hydrophobic phase and the hydrophilic phase with one another.

12. The method of claim 11, wherein the method further comprises heating the hydrophobic phase and the hydrophilic phase with one another at a temperature of about 60° C. to about 90° C., optionally about 70° C. to about 80° C., further optionally about 70° C. to about 75° C.

13. The method of claim 11, further comprising maintaining a pH of from about 4 to about 5.

* * * * *